US007459125B1

(12) United States Patent
Stankov et al.

(10) Patent No.: US 7,459,125 B1
(45) Date of Patent: Dec. 2, 2008

(54) DEVICE FOR DETERMINING AN ANALYTE IN A LIQUID SAMPLE

(75) Inventors: Milovan Stankov, Alencon (FR); Raphael Donati, Radon (FR)

(73) Assignee: Vedalab, Alencon (FR)

( * ) Notice: Subject to any disclaimer, the term of this patent is extended or adjusted under 35 U.S.C. 154(b) by 82 days.

(21) Appl. No.: 09/720,862

(22) PCT Filed: Jun. 10, 1999

(86) PCT No.: PCT/FR99/01380

§ 371 (c)(1), (2), (4) Date: Jan. 2, 2001

(87) PCT Pub. No.: WO00/00288

PCT Pub. Date: Jan. 6, 2000

(30) Foreign Application Priority Data

Jun. 30, 1998 (FR) .................................. 98 08480

(51) Int. Cl.
*G01N 31/22* (2006.01)
*G01N 33/53* (2006.01)

(52) U.S. Cl. ............................ 422/56; 422/55; 422/58; 422/61; 436/65; 436/510; 435/806

(58) Field of Classification Search .................. 422/50, 422/55, 56, 57, 58, 61, 68.1; 436/65, 510; 435/806

See application file for complete search history.

(56) References Cited

U.S. PATENT DOCUMENTS 4,774,192 A * 9/1988 Terminiello et al. ......... 436/530
5,611,995 A 3/1997 De Zoeten et al.
5,980,828 A * 11/1999 McClintock et al. .......... 422/58
6,140,136 A * 10/2000 Lee ............................ 436/518
6,150,178 A * 11/2000 Cesarczyk et al. .......... 436/165
6,365,417 B1 * 4/2002 Fleming et al. ............. 436/514
6,372,514 B1 * 4/2002 Lee ............................ 436/518
6,555,390 B2 * 4/2003 Chandler .................... 436/518

FOREIGN PATENT DOCUMENTS

| | | | |
|---|---|---|---|
| EP | 0 291 194 | A1 | 11/1988 |
| EP | 0 306 336 | A2 | 3/1989 |
| EP | 0 560 411 | A2 | 9/1993 |
| JP | 7-27761 | A | 1/1995 |
| WO | WO 95/08761 | A1 | 3/1995 |
| WO | WO 97/26083 | A1 | 7/1997 |
| WO | WO 98/00712 | A1 | 1/1998 |

* cited by examiner

*Primary Examiner*—Jill Warden
*Assistant Examiner*—Paul S Hyun
(74) *Attorney, Agent, or Firm*—Oliff & Berridge, PLC

(57) ABSTRACT

The invention concerns a device for determining an analyte in a liquid sample, comprising: a) a gripping support (1); b) first capillary diffusing means (2) integral with the gripping support (1) comprising a downstream zone (2a) accessible to external observation; c) a set of predetermined reagents for detecting and/or quantifying the analyte; d) a member for collecting (4) the liquid sample mounted on the support (1). The invention is characterized in that the member for collecting (4) the liquid sample is mounted mobile or fixed on the support; second capillary diffusion means (41) extends from a zone collecting (41a) said sample, to a zone transferring (41b) the latter; and an upstream zone (2b) of said first capillary diffusion means (2) is arranged to be urged temporarily to constitute continuous capillary flow with the second diffusion means (41) transferring zone (41b), when the collecting member (4) is in the retracted position.

11 Claims, 2 Drawing Sheets

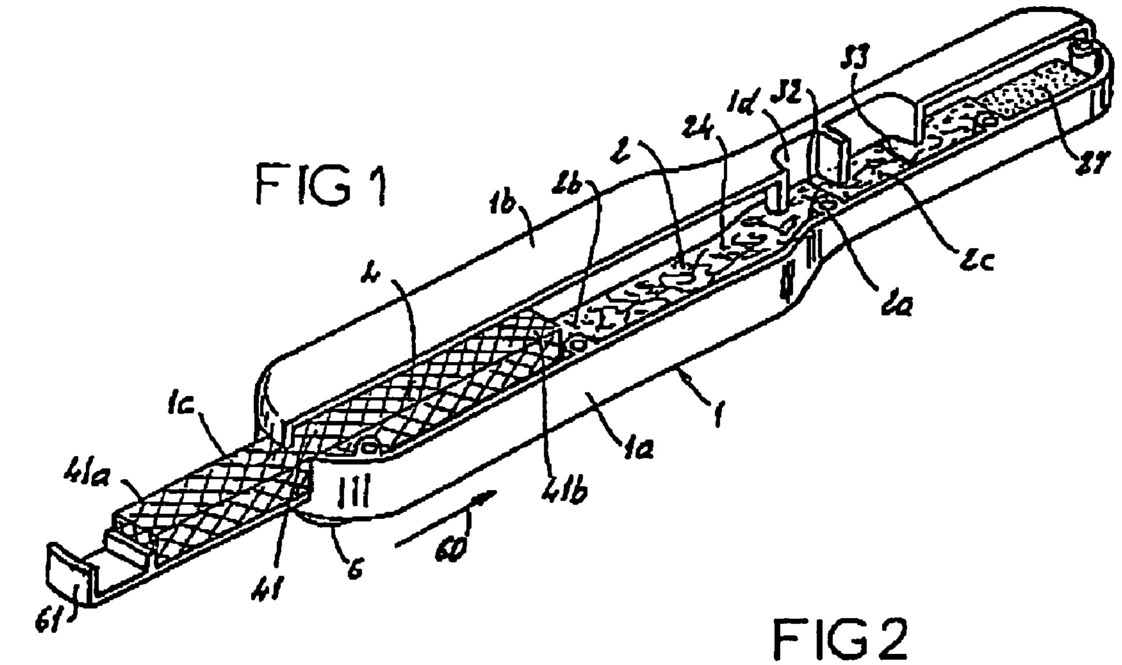
FIG 1
FIG 2
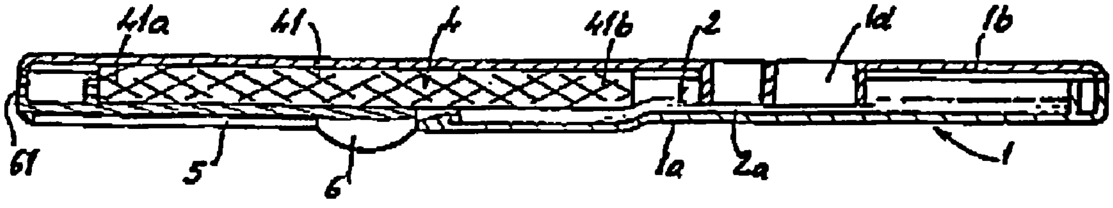
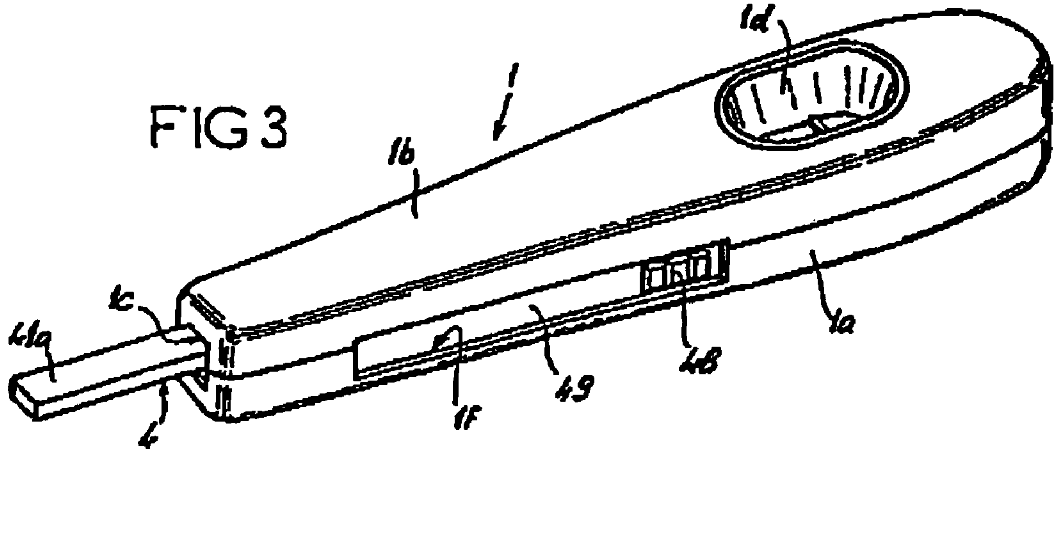
FIG 3

FIG 4
FIG 6
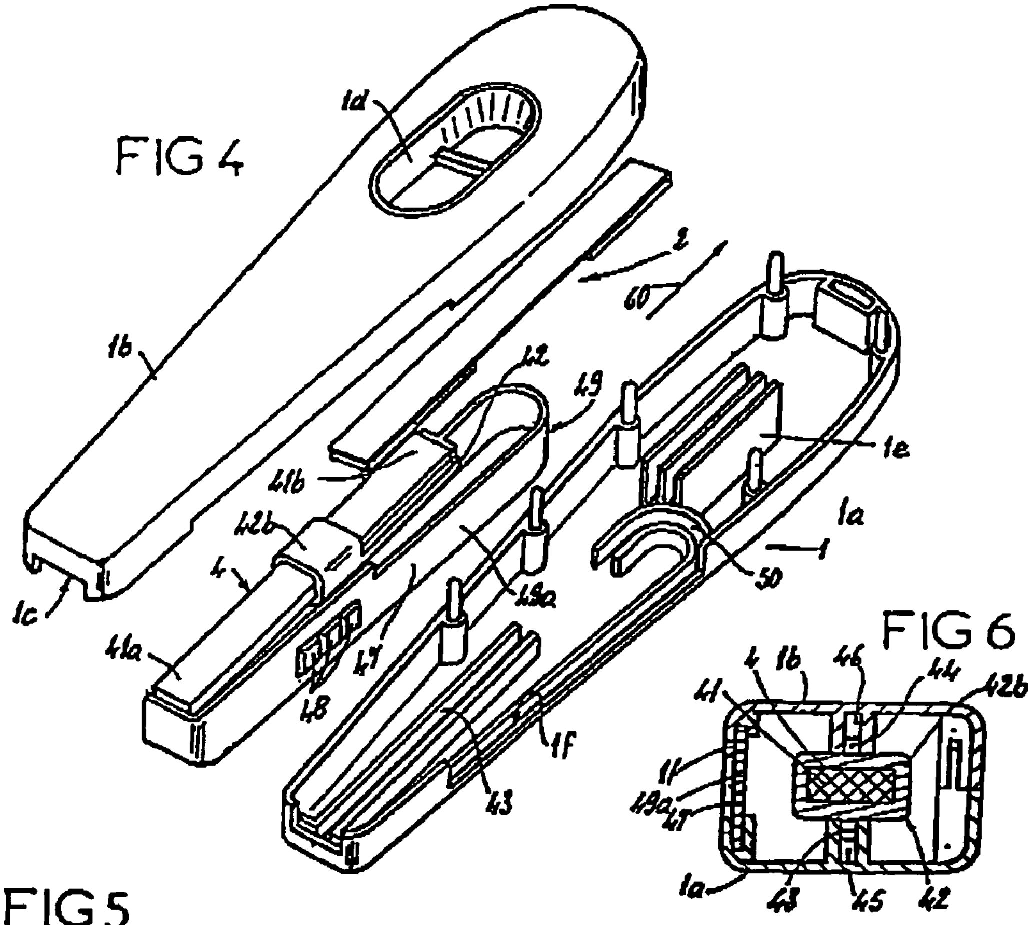
FIG 5
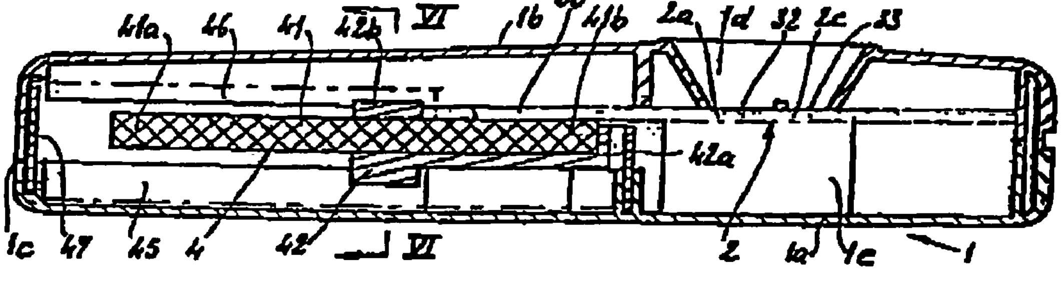
FIG 7
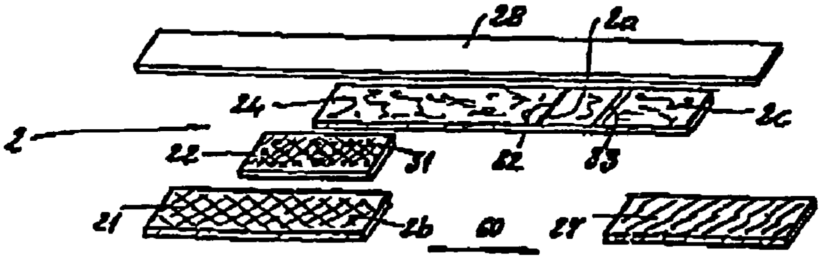

DEVICE FOR DETERMINING AN ANALYTE IN A LIQUID SAMPLE

This nonprovisional application claims the benefit of PCT/FR99/01380 filed Jun. 10, 1999 and FR98 08480 filed Jun. 30, 1998 in France.

The present invention relates to a device for determination of an analyte present in a liquid sample.

The term "analyte" is intended to mean any chemical, biochemical or biological entity which it is desired to determine, that is to say identify or detect, and/or quantitatively analyze and/or measure.

By way of preference, and not exclusively, the present invention will be introduced, defined and described with reference to the determination of a biological entity, in particular a hormone, for example the hormone HCG which makes it possible to detect the condition of pregnancy in a woman.

The term "liquid sample" is intended to mean any sample in which the analyte in question is in solution or suspension, as it is directly applied or treated by the determination device which will be discussed below. This liquid sample may itself have been obtained from a withdrawal or other sample containing the analyte, for example a bodily fluid, by physical and/or chemical and/or biological treatment. This means, in particular, that the dissolving or dispersing medium corresponding to the liquid sample is not necessarily aqueous.

In accordance with FIGS. 8 and 9 of document EP-A-0 291 194, a device for determination of an analyte, in particular for the determination of the HCG hormone, and which corresponds to the following general description, has been described.

A device of this type comprises:

a) a support to be gripped, which is in kit form, comprising an opening at one end for the passage of the second capillary diffusion means which will be discussed below, protruding from the end of the kit and having a zone for collection of a liquid sample; on the opposite side from the take-up component, this kit includes a window registered with at least the downstream zone of the first capillary diffusion means which will be discussed below;

b) said first means for capillary diffusion in a reference direction and sense, integral with and fixed in the support to be gripped, comprising a downstream zone which is accessible to external observation, by virtue of the aforementioned window registered with said downstream zone;

c) a set of predetermined reagents for the detection and/or quantitative analysis of the analyte, comprising:

- a first reagent comprising a visible and/or mensurable marker, this first reagent being arranged in the free state in an upstream zone of the first capillary diffusion means;
- and a second reagent, fixed, that is to say immobilized, in the downstream zone of the first capillary diffusion means, for direct or indirect capture of the first reagent;

d) said second capillary diffusion means having the shape of a rigid stick, mounted and integral with the support to be gripped in such a way as to permanently establish, in the kit, capillary flow continuity, from the collection zone of the second capillary diffusion means to the upstream zone of the first capillary diffusion means, then from the latter to the downstream zone of the first capillary diffusion means, e) and a removable cap, for protection of the projecting part of the second capillary diffusion means, and more precisely its collection zone.

The way in which the device described above functions can be deduced from the following description.

The user removes the cap, then places the liquid sample, for example a stream of urine, in direct contact with the collection zone of the second capillary diffusion means. The liquid sample firstly migrates, in the reference direction, toward the upstream zone of the first capillary diffusion means, in which, on the one hand, it entrains the first reagent and, on the other comprising an end zone for collecting the liquid sample, protruding out of the kit; the kit also comprises, at the opposite end to a part allowing it to be handled, a window in register with the downstream zone of the first capillary diffusion means; the moving member can be moved with respect to the support to be gripped, from a starting position in which the liquid sample collection zone of the moving member can be brought into contact with this sample, and in which the window in the kit is concealed by the support to be gripped, out of the support to be gripped, into an irreversible retracted position in which the aforementioned collection zone is contained and wholly incorporated in the support to be gripped, and in which the window of the kit is in register with that of the support to be gripped, which makes the downstream zone of the first capillary diffusion means accessible for viewing.

Although this is not expressly described in document WO-A-97/26 083, the aforementioned device requires a removable means for protecting the collection zone of the second capillary diffusion means when the moving member is in the starting position in which the collection zone protrudes out from the support to be gripped. This is because, bearing in mind the additional means provided, on the one hand, on the moving member or kit, for example notches and, on the other hand, on the support to be gripped, for example tabs fully engaging in the aforementioned notches, the retracted position is irreversible, as stated above.

The way in which the aforementioned device works can be deduced from its structure:

- the means protecting the collection zone is removed, to obtain a device ready for use, with its collection zone protruding,
- once the liquid sample has been collected, the moving member is brought into the retracted position, hand, structural, that is to say permanent capillary flow continuity of the liquid sample from the second capillary diffusion means to the first capillary diffusion means.

In both instances, it is necessary to provide a removable means for protecting the collection zone of the second capillary diffusion means in its starting position, that is to say in the position in which it protrudes for taking the liquid sample.

The subject of the present invention is a device like the aforementioned one that makes it possible to dispense with the additional removable means for protecting the liquid sample collection zone while at the same time isolating this zone from the outside of the device while the device is not in use, that is to say being used or set for taking a liquid sample, then reading the result regarding the analyte.

In accordance with the invention and with respect to document EP-A-0 291 194, the device comprises a member for taking up the liquid sample, to which is secured the second capillary diffusion means, to the exclusion of the first capillary diffusion means. This take-up member is mounted so that it can be moved relative to the support to be gripped, for example in translation, between two extreme positions, namely:

- one which protrudes from the support to be gripped, in which, on the one hand, the liquid sample collection zone belonging to the second capillary diffusion means can be brought into contact with this sample, outside the support to be gripped and, on the other hand, a transfer zone of the second capillary diffusion means, at the opposite end to the collection zone, is not in capillary flow continuity and is therefore isolated from the upstream zone of the first capillary diffusion means, and the other which is retracted with respect to the support to be gripped and in which, on the one hand, the transfer zone of the second capillary diffusion means is, removably or temporarily, in capillary flow continuity with the upstream zone of the first capillary diffusion means and, on the other hand, the collection zone of the second capillary diffusion means is contained in the support to be gripped.

In consequence, by comparison with documents EP-A-0 291 194 and WO-A-97/26083, the device according to the invention is characterized by the dissociation of the two capillary diffusion means and by the possibility of temporarily isolating these two means with respect to the capillary flow of the liquid sample.

What is more, by comparison with document WO-A-97/26083, the device according to the invention is characterized, aside from all of the predetermined reagents chosen for detecting and/or quantifying the analyte, in that the first capillary diffusion means remains on the same side as the support to be gripped, and that the take-up member is therefore essentially concerned with taking the liquid sample.

The solution according to the invention also affords decisive advantages.

The possibility of isolating the two capillary diffusion means from the flow of liquid makes it possible to separate and to sequence the actual sampling and the reaction or reactions required for detecting and/or quantifying the analyte, namely makes it possible to take said sample before or after performing the reactions.

This is important in order to avoid starting the required reaction or reactions before having allowed a maximum or optimum amount of liquid sample for analysis to be taken.

Moving the second capillary diffusion means some distance away from the first capillary diffusion means makes it possible, for a given device length or size, to have a larger length available for collecting the liquid sample, when said device is in the protruding position.

A device according to the invention can be used with any sort of reagents predetermined on the basis of the relevant analyte in the liquid sample, on the one hand, and the operating protocol adopted for the determination, on the other hand.

The term reagent is intended to mean any chemical, biochemical or biological entity capable of binding with the analyte and/or another reagent.

The term "bind" or "bond" is intended to mean any strong bond, for example a covalent bond, or weak bond, for example of the antigen/antibody or avidin/streptavidin type.

Preferably, but not exclusively, the reagents in question according to the invention are biological entities, of the liquid or antiligand type, this being with respect to the analyte or another reagent of the biological type. This category comprises reagents such as antibodies, antigens, haptens, avidin/streptavidin, as well as peptides, proteins and polynuclotides.

By way of example, the first and second reagents are respectively two identical or different specific monoclonal antibodies directed against the analyte.

The term "marker" is intended to mean any physical, chemical, biochemical or biological entity directly or indirectly making it possible to determine the first reagent, in particular when it is bound directly or indirectly to the analyte. A marker of this type, known per se, may for example be an enzyme or alternatively metallic particles, for example gold particles, obtained for example from colloidal gold.

According to the invention, the first reagent is deposited on the second capillary diffusion means, in particular downstream of the collection zone of the take-up component, or alternatively the first reagent is deposited on the first capillary diffusion means, in particular downstream of the upstream zone of said first means, but upstream of the downstream zone accessible to external operation.

In a manner which is known per se, the set of reagents which are predetermined on the basis of the analyte and the determination protocol may be implemented according to a variety of formats:

- according to a sandwich format, the first and second reagents being predetermined to bind respectively and specifically with the analyte, for example on two identical or different epitopic sites of the analyte, when it consists of a biological molecule;
- according to a competition format, the first reagent or the second reagent being predetermined identically with or in similar fashion to the analyte, to bind with the other reagent, in competition with the analyte.

Furthermore, in the case of an analyte consisting of a biological entity comprising two ligands, which can bind respectively with the first reagent and a third reagent, the latter is deposited in the free state on a porous support, in the case in point the second capillary diffusion means or the first capillary diffusion means, at a point functionally upstream of the downstream zone of the first diffusion means. The second reagent is also predetermined in order to capture the third reagent.

In order to check that the reaction or reactions needed for the determination of the analyte have actually taken place, another reagent predetermined to bind directly or indirectly with the first reagent is fixed in a zone which is adjacent to but downstream from the downstream zone of the first diffusion means, this adjacent zone also being accessible to external observation.

By way of example, the first reagent comprises a particulate marker, for example, gold particles, which are visible and/or measurable directly when it is concentrated in the downstream zone of the first diffusion means.

The present invention will now be described with reference to the appended drawings, in which:

FIG. 1 is a perspective representation, with partial cut away, when the take-up component is in the protruding position, of a device according to a first embodiment of the invention;

FIG. 2 represents the device represented in FIG. 1, in longitudinal and vertical section, when the take-up component is in the retracted position;

FIG. 3 represents a perspective view, when the take-up component is in the protruding position, of a device according to a second embodiment of the invention;

FIG. 4 represents an exploded perspective view of the device represented tin FIG. 3, when the take-up component is in the retracted position;

FIG. 5 represents a view in longitudinal and horizontal section of the device represented in FIG. 4, when the take-up component is in the retracted position;

FIG. 6 represents a view in cross section, level with the component 42*b* for holding the stick 41 in position, of the device represented in FIGS. 4 and 5;

FIG. 7 represents an exploded view of the first capillary diffusion means, identical for the two embodiments of the invention, and employed in the same position, as shown in FIGS. 1 and 2 in particular.

According to FIGS. 1 and 2, a device according to the invention comprises:

- a support 1 to be gripped, which is in the form of a kit and comprises, at a distal end, an opening 1*c* for the take-up component 4 described below to pass through into the protruding position, and on the opposite side from this end, a window 1*d* registered with at least one downstream zone 2*a* of the first capillary diffusion means 2 described below;
- the first of the two capillary diffusion means having the form of a multilayer wad, integral with the support 1 to be gripped and comprising the downstream zone 2*a* which is accessible to external observation; this first means is more particularly represented in an exploded view in FIG. 2, and will be described in more detail below;
- a set of reagents predetermined for the detection and/or quantitative analysis of the analyte, comprising at least
  - a first reagent 31, comprising a visible and/or measurable marker, this first reagent being arranged in the free state on the first diffusion means 2, in particular downstream of the upstream zone 2*b* which will be discussed below;
  - and a second reagent 32, fixed in the downstream zone 2*a* of the first diffusion means 2, for the direct or indirect capture of the first reagent;
  - another reagent 33, predetermined to bind with the first reagent 31 and fixed in a zone 2*c*, adjacent to but downstream of the aforementioned downstream zone 2*a* of the first diffusion means 2, this adjacent zone also being accessible to external observation, for example with the same window 1*d* of the kit 1;
- a component 4 which is intended to take up the liquid sample and is mounted removably on the support 1, or vice versa; this component 4 includes a second means 41 for capillary diffusion, in the same direction and the same sense 60 as those determined by the first capillary diffusion means 2; this second means 41 extends from the zone 41*a* for collection of the sample to be zone 41*b* for transfer of the latter; this take-up component 4 can be moved and be translated, relative to the support 1 to be gripped, between two positions, namely one (cf. FIG. 1) which protrudes with respect to said support to be gripped, in which the collection zone 41*a* can be brought into contact with the liquid sample, outside the support to be gripped, and in which the transfer zone (41*b*) is not in capillary flow continuity with and is therefore isolated from the upstream zone (2*b*) of the first capillary diffusion means (2), and the other which is retracted (cf. FIG. 2), in which the collection zone 41*a* is contained in said support to be gripped, and in which the transfer zone (41*b*) of the second capillary diffusion means (41) is, removably, that is to say temporarily, in capillary flow continuity with the upstream zone (2*b*) of the first capillary diffusion means (2); this explains the fact that the take-up component 4 and the support 1 to be gripped are elongated in the translation direction.

In correspondence with the general structure described above:

- the upstream zone 2*b* of the first capillary diffusion means 2 is designed to come removably or temporarily into capillary flow continuity with the transfer zone 41*b* of the second capillary diffusion means 41, when the take-up component 4 is in the retracted position, and to be isolated from the same capillary flow with respect to the same transfer zone 41*b*, when the take-up component 4 is in the protruding position;
- and the first reagent 31 is deposited in the free state on the first diffusion means 2, as described above, in a zone 2*a* downstream of the upstream zone 2*b*; of course, however, the first reagent may be deposited directly in the upstream zone 2*b* of the first capillary diffusion means 2, or else directly on the second capillary diffusion means 41.

In order to actuate the displacement of the take-up component 4, as shown in FIG. 2, the support 1 to be gripped includes a longitudinal slideway 5, whose shape is adapted to the path along which said component 4 moves, and the latter includes a manual control component 6 passing through this slideway. The travel of the component 6 in the slideway 5 determines the two extreme positions of the take-up component 4, and as shown in FIG. 2, has a length greater than the length of overlap of the transfer zone 41*b* of the second capillary diffusion means 41 and the upstream zone (2*b*) of the first capillary diffusion means, when the device is in the retracted position.

As shown more particularly by FIG. 7, the first capillary diffusion means 2 is obtained by assembling a variety of sections or pieces, themselves fixed on a transparent plastic band 28, and in permanent capillary flow continuity once they have been assembled together.

According to FIG. 7, and in the sense and direction 60 of the capillary flow, further to the transparent band 28, the first capillary diffusion means 2 includes:

- a first section 21 of relatively high porosity, for example made of cellulose, with a pore size of between 2 μm and 50 μm, designed to come into capillary flow continuity with the transfer zone 41*b* of the second capillary diffusion means 41; it is this section which constitutes the upstream zone 2*b* of the first diffusion means 2;
- a section 22 consisting, for example, of glass fiber, having a pore size of between 2 μm and 500 μm, on which the first reagent 31 is deposited in the free state;
- a section 24 of relatively low porosity, for example consisting of nitrocellulose, with a pore dimension of between 1 μm and 30 μm, including both the downstream zone 2*a* in which the second reagent 32 is fixed and the adjacent zone in which the other reagent 33 is fixed, these two zones being accessible to external observation through the window registered 1*d* of the kit 1;
- a section 27, consisting for example of cellulose, having a pore dimension of between 2 μm and 50 μm, for the reception by absorption of all the liquids which have flowed over the first capillary diffusion means 2, beyond the downstream zones 2*a*; this reception section is therefore integral with the support 1 to be gripped, and arranged downstream of and in capillary flow continuity with the downstream zone 2*a* of the first capillary diffusion means 1.

The device according to FIGS. 3 to 5 has the same general structure as the one defined above. The same numerical references identify parts or components which have the same function as that described with reference to FIGS. 1 and 2. Only the following differences will be described below.

The take-up component 4 comprises a carriage 42 for supporting the second capillary diffusion means 41, contained in the kit 1 or support to be gripped. The latter and the carriage 42 include means for guiding said carriage as it moves, these means being more particularly visible in FIG. 6, and consisting of two slideways 45 and 46 corresponding to the kit 1, one being an upper slideway and the other being a lower slideway, and the two being aligned, and of two corresponding ribs 43 and 44 corresponding to the carriage 42 and sliding in the slideways 45 and 46, respectively.

The second diffusion means 41 is in the form of a relatively rigid stick, and the carriage 42 includes a rear stop 42*a* relative to the sense in which said carriage moves, and a component 42*b* for holding the stick 41 in position and is in the form of a ring.

The kit 1 also incorporates a means 47 for actuating the carriage 42, with a manual control 48. More precisely, the actuation means 47 comprises a hairpin-shaped semirigid band 49, one branch 49*a* of which has a component 4 to be gripped on its outer face, and the other branch of which has an end joined to the carriage 42. In correspondence, the kit 1 comprises a path 50 which is intended for guiding and pulling the band and is also shaped as a hairpin, and on the other hand a window 1*f* which is designed for the passage of the component 48 to be gripped, and whose length is adapted to the displacement travel of the take-up component 4. As clearly shown by comparing FIGS. 4 and 5, this travel is far longer than the length of overlap of the transfer zone 41*b* of the second capillary diffusion means 41 and the upstream zone 2*b* of the first capillary diffusion means 2, when the device is in the retracted position.

In consequence, when the component 48 to be gripped is pushed toward the proximal end of the kit 1, as shown in FIG. 3, the band 49 moves in the guide path 50 and pushes the carriage 42 toward the position in which the take-up component 2 protrudes. In the reverse sense, the carriage 42 is moved to the position in which the take-up component 4 is retracted.

As also shown by FIGS. 4 and 5, the first capillary diffusion means 2 is clamped and held inside the kit, between ribs 1*e* extending parallel to the direction 60 of the capillary flow.

The way in which a device according to the invention operates can be derived from the preceding description:

- initially, that is to say before use, the take-up component 4 is in the retracted position (cf. FIGS. 2 and 4), so that the kit 1 is a closed entity, with the exception of the window 1*d*; in the case in FIGS. 1, it is a flap 61, integral with the proximal end of the take-up component 4, which closes the opening 1*c*; and in the case of FIGS. 4 and 5, it is the opposite end of the semirigid band 49 from the carriage 42 which closes the opening 1*c* (cf. FIG. 5);
- by means of the control component 6 or 48, the user brings the take-up component 4 into the protruding position, in which a flow or liquid sample containing the analyte is brought into contact with the collection zone 41*a;*
- using the same hand, the same take-up component is returned into the retracted position, with the opening 1*c* being closed, as described above;
- it is only in the latter position, without further intervention by the user, that the liquid sample migrates successively from the second capillary diffusion means 41 to the first capillary diffusion means 42, and from upstream to downstream on the latter; the reactions generated by the reagents which have been described above take place; the result is accessible to external observation through the window 1*d*, for example with the naked eye;
- the determination device, which is a single-use device, can then be disposed of, in the retracted position in FIGS. 2 and 4.

According to FIG. 5, in relation to the sense of observation through the window 1*d*, it will be observed that the transfer zone 41*b* of the second capillary diffusion means 41 comes below the upstream zone 2*b* of the first capillary diffusion means 2, when the take-up component 4 is in the retracted position, and this promotes the capillary flow at the junction between the two capillary diffusion means 2 and 41, when the take-up component 4 is in the retracted position.

The invention claimed is:

1. A device for determination of an analyte in a liquid sample, comprising:

a) an elongated support to be gripped extending along a reference direction having a proximate gripping zone and a distal portion away from said gripping zone;

b) a first means for capillary diffusion in said reference direction, integral with the support to be gripped, comprising a downstream zone which is accessible to external observation, and an upstream zone opposite to said downstream zone along said reference direction;

c) a movable member movably mounted inside said support along said reference direction, for taking up the liquid sample, comprising a second means for capillary diffusion extending in said reference direction having a distal collection zone for collecting said sample, and a proximal transfer zone opposite to said distal collection zone along said reference direction, said movable member being mounted on said support so that it can move between a protruding position and a retracted position, wherein:

in the protruding position, the distal collection zone of the second means for capillary diffusion protrudes from the distal portion across an opening of said support to be brought into direct contact with said sample at said distal portion of said support, and in which the transfer zone of the second means for capillary diffusion remains inside said support and is in capillary flow discontinuity with, and away from, the upstream zone of the first means for capillary diffusion, and in the retracted position, the transfer zone of the second means for capillary diffusion is in capillary flow continuity, inside said support, with the first means for capillary diffusion, and in which the collection zone of the second means for capillary diffusion is contained in said distal portion of said support, leaving said opening across said support free of said second means for capillary diffusion;

d) means for opening and closing said opening in said support, respectively in the protruding and retracted positions of said movable member;

e) a set of predetermined reagents for at least one of detection and quantitative analysis of the analyte, comprising a first reagent comprising a marker, being arranged in the free state on any one of the first and the second capillary means for capillary diffusion in a functional location upstream of the downstream zone of the first means for capillary diffusion, and a second reagent, fixed in the downstream zone of the first means for capillary diffusion, for direct or indirect capture of the first reagent.

2. The device as claimed in claim 1, wherein the first reagent is deposited on the second means for capillary diffusion downstream of the collection zone.

3. The device as claimed in claim 1, wherein the first reagent is deposited on the first means for capillary diffusion downstream of said upstream zone.

4. The device as claimed in claim 1, wherein the support to be gripped is in the form of a kit which, at one end, comprises an opening for the movable member to pass through into the protruding position, and on the opposite side from said end, a window registered with at least the downstream zone of the first means for capillary diffusion.

5. The device as claimed in claim 1, wherein the support to be gripped includes a slideway whose shape is adapted to the path along which the movable member moves, and said movable member includes a manual control component passing through said slideway.

6. The device as claimed in claim 1, wherein the movable member can be moved and be translated relative to the support to be gripped, and said movable member and said support are elongated in the translation direction.

7. The device as claimed in claim 1, wherein the first means for capillary diffusion includes two separate sections, in permanent capillary flow continuity, including a first section of relativity high porosity, designed to come removably into capillary flow continuity with the transfer zone of the second means for capillary diffusion, and a second section of relatively low porosity, including said downstream zone.

8. The device as claimed in claim 4, wherein the movable member comprises a carriage for supporting the second means for capillary diffusion, the kit and the carriage includes means for guiding said carriage as it moves, and the kit incorporates a means for actuating said carriage, with manual control.

9. The device as claimed in claim 8, wherein the second means for capillary diffusion is in the form of a stick, and the carriage includes a rear stop relative to the direction of movement, and a component for holding said stick in position.

10. The device as claimed in claim 8, wherein the actuation means comprises a hairpin-shaped semirigid band, one branch of which has a component to be gripped on its outer face, and the other branch of which has an end joined to the carriage, and wherein the kit comprises, on the one hand, a path which is intended for pulling the band and is also shaped as a hairpin, and on the other hand a window which is designed for the passage of the component to be gripped, and whose length is adapted to the displacement travel of the movable member.

11. The device as claimed in claim 4, wherein the first means for capillary diffusion is clamped and held inside the kit, between ribs extending parallel to the direction of the capillary flow.

* * * * *